(12) United States Patent
Denzler et al.

(10) Patent No.: US 10,505,207 B2
(45) Date of Patent: Dec. 10, 2019

(54) METHOD SENSOR AND REGULATION APPARATUS FOR REGULATING GAS OPERATED ENERGY CONVERTER PLANTS

(71) Applicants: Hexis AG, Winterthur (CH); MEMS AG, Birmensdorf (CH)

(72) Inventors: Roland Denzler, Weisslingen (CH); Philippe Pretre, Daettwil (CH); Andreas Kempe, Zurich (CH)

(73) Assignee: Hexis AG, Winterthur (CH)

( * ) Notice: Subject to any disclaimer, the term of this patent is extended or adjusted under 35 U.S.C. 154(b) by 0 days.

(21) Appl. No.: 14/289,953

(22) Filed: May 29, 2014

(65) Prior Publication Data
US 2014/0356751 A1 Dec. 4, 2014

(30) Foreign Application Priority Data

May 29, 2013 (EP) ..................................... 13169741

(51) Int. Cl.
*H01M 8/04* (2016.01)
*H01M 8/04089* (2016.01)
(Continued)

(52) U.S. Cl.
CPC ........ *H01M 8/04089* (2013.01); *F23N 5/006* (2013.01); *G01F 1/68* (2013.01);
(Continued)

(58) Field of Classification Search
CPC . H01M 8/04089; H01M 8/04746; G01F 1/68; F02D 19/029; F02D 41/0027;
(Continued)

(56) References Cited

U.S. PATENT DOCUMENTS

| | | | |
|---|---|---|---|
| 3,606,790 A * | 9/1971 | Matsumoto | G01N 27/18 |
| | | | 73/23.32 |
| 5,401,162 A * | 3/1995 | Bonne | F23N 1/022 |
| | | | 431/12 |

(Continued)

FOREIGN PATENT DOCUMENTS

| | | |
|---|---|---|
| EP | 1 265 068 A1 | 12/2002 |
| EP | 2 015 056 A1 | 1/2009 |

(Continued)

OTHER PUBLICATIONS

D. Matter, B. Kramer, T. Kleiner, B. Sabbattini, T. Suter, "Mikroelecktronischer Haushaltsgaszahler mit neur Technologie"(Microelectronic household gas meter using new technolgoies), Technisches Messen 71, 3 (2004), pp. 137-146 (partial oral translation by J. Koytcheff on May 2, 2017).*

(Continued)

*Primary Examiner* — Stewart A Fraser
*Assistant Examiner* — Victoria H Lynch
(74) *Attorney, Agent, or Firm* — Kilpatrick Townsend & Stockton LLP

(57) ABSTRACT

A method for the combined controlled regulation of fuel gas-oxygen carriers of a gas operated energy converter plant (15), in particular of a fuel cell plant, is provided in which the mass or volume through flow of the fuel gas (1) and/or of the oxygen carrier (2) is detected in order to regulate the mixing ratio (r) of fuel gas to oxygen carrier. In the method at least two physical parameters of the fuel gas are additionally determined using a micro thermal sensor (3.1, 3.2), for example, the mass flow and/or volume through flow of the fuel gas and the thermal conductivity or thermal capacity of the fuel gas are determined and a desired value for the mixing ratio is determined from the physical parameters which depends on the fuel gas or on the composition of the (Continued)

Figure 1:
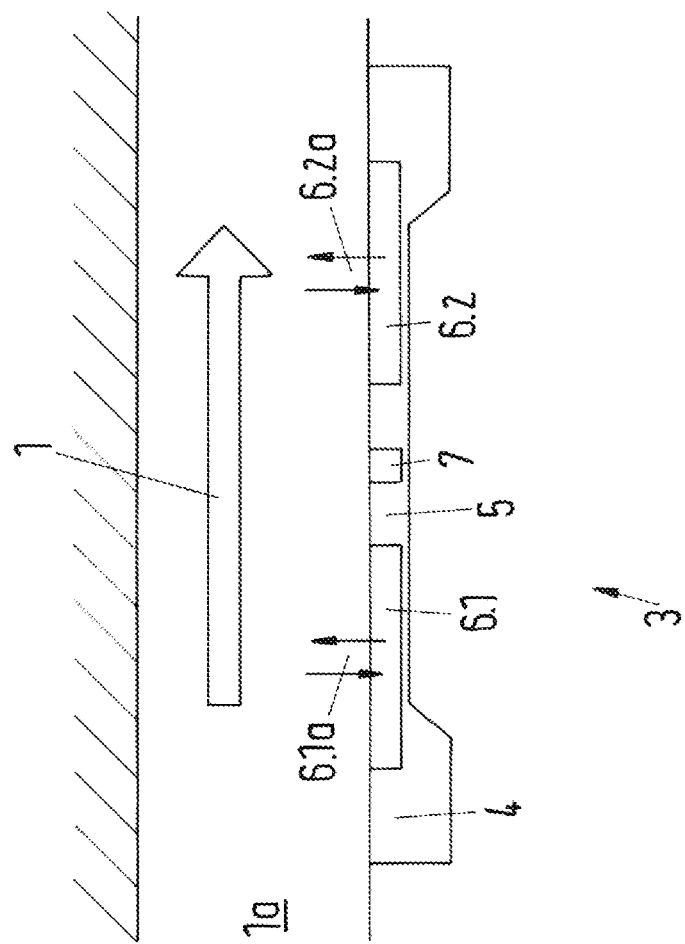

fuel gas, and which desired value is used for the regulation of the mixing ratio.

13 Claims, 9 Drawing Sheets

(51) Int. Cl.
G01F 1/68 (2006.01)
G01N 33/22 (2006.01)
H01M 8/0438 (2016.01)
H01M 8/0444 (2016.01)
H01M 8/04746 (2016.01)
F23N 5/00 (2006.01)
H01M 8/124 (2016.01)

(52) U.S. Cl.
CPC ...... *G01N 33/225* (2013.01); *H01M 8/04388* (2013.01); *H01M 8/04395* (2013.01); *H01M 8/04447* (2013.01); *H01M 8/04455* (2013.01); *H01M 8/04753* (2013.01); *H01M 2008/1293* (2013.01); *Y02E 20/14* (2013.01)

(58) Field of Classification Search
CPC ........... F02D 41/187; F02D 2200/0611; F02D 2200/0612; F02D 21/00; F02D 19/12; F02D 19/081; F02D 19/087; F02B 2043/103; F02M 21/0215; C01B 3/00
USPC ............. 429/444; 123/527, 528, 529, 406.3; 423/648
See application file for complete search history.

(56) References Cited

U.S. PATENT DOCUMENTS

2006/0179936 A1* 8/2006 Matter .................. G01F 1/6965
73/195
2011/0137540 A1* 6/2011 Mai ....................... F02D 41/004
701/103

FOREIGN PATENT DOCUMENTS

EP        2 574 918 A1    4/2013
WO    WO 2011012758 A2 *  2/2011  ............... G01F 1/68

OTHER PUBLICATIONS

European Search Report dated Oct. 11, 2013, from European Application No. 13169741.9 (6 pages).

* cited by examiner

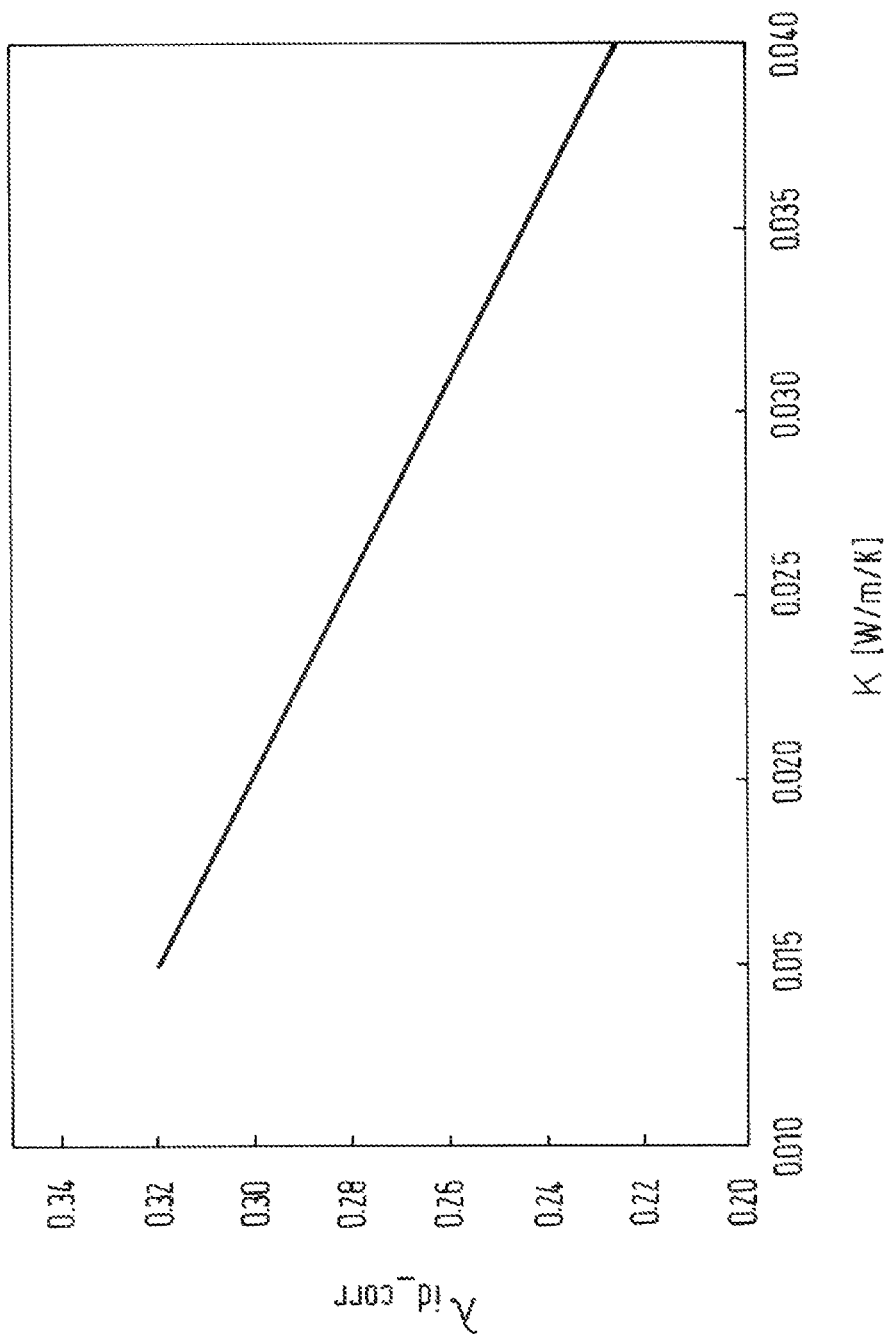

METHOD SENSOR AND REGULATION APPARATUS FOR REGULATING GAS OPERATED ENERGY CONVERTER PLANTS

CROSS-REFERENCE TO RELATED APPLICATION

This application claims priority to European Patent Application No. 13169741.9, filed May 29, 2013, the disclosure of which is incorporated by reference herein.

The invention relates to a method for regulating gas operated and, in particular natural gas operated, energy converter plants in accordance with the preamble of claim 1, as well as to a thermal sensor and to a regulation apparatus for regulating gas operated and, in particular natural gas operated, energy converter plants in accordance with the preamble of claims 8 and 12.

For example cogeneration plants (CHP), fuel cell plants, in particular fuel plants having high temperature fuel cells of the SOFC type ("Solid Oxide Fuel Cell") which are operated at 700° C. to 960° C., heating devices respectively gas furnaces, warm water generators, gas operated heat pumps and current generation plants, as well as combinations thereof are classified as energy converter plants. It is true for all these plants that an efficient energy conversion and an energy conversion low in emission depends on whether the process specific ideal quantity of oxygen carrier is supplied to the fuel gas. As a process this can relate to the reformation, partial oxidation as well as the complete oxidation of the fuel gas. If, for example, the oxygen of air serves as an oxygen carrier for the complete oxidation in a combustion motor, then in the conversion process (reforming, partial oxidation) of a fuel cell the oxygen carrier can also be air, water, carbon oxide or a mixture of the three mentioned oxygen carriers, such as e.g. for the anode gas recirculation.

The ideal quantity of oxygen carrier depends on the composition of the fuel gas, this means on the fuel gas quality. Considerable deviations in the fuel gas quality can arise in dependence on the region of application and the supplier and one can only react on these deviations in the knowledge thereof. During the conversion process (reforming, partial oxidation) an excess of oxygen carriers leads to an inefficient process, which runs too hot, in contrast to which a too small quantity of the oxygen carrier leads to a reduced fuel gas conversion and finally to sooting. In the end both situations lead to an instable process or to a damaging and/or a shortening of the life time of the plant.

The object of supplying oxygen carriers to the fuel gas is generally taken over by a combined controlled regulation of fuel gas-oxygen carriers, which in the case of air as an oxygen carrier, is referred to as the combined controlled regulation of fuel gas-air. However, without the knowledge on the fuel gas quality, the dosage of the ideal quantity is not possible. A fixed mixing ratio must therefore be selected in such a way that the deviations in the fuel gas quality under no circumstances lead to a damaging of the plant, whereby one loses efficiency for a "good" fuel gas quality, since a safety margin has to be maintained with respect to the ideal value.

One refers to the ratio of oxygen carrier to fuel gas in comparison to a stoichiometric mixture at which the theoretically required oxygen carrier quantity is present for a complete combustion, this means $\lambda=1$ as a lambda value $\lambda$ or, in the case of air as an oxygen carrier, as an air number. If one refers to the ideal ratio of oxygen carrier to fuel gas quantity for an aspired oxygen process with $\lambda_{id}$ then for an ideal mixing ratio $r_{id}$ this results in $$r_{id} = L_{min} \cdot \lambda_{id} \qquad (1)$$

where $L_{min}$ means the ideal oxygen carrier quantity for a $\lambda=1$ combustion. In the case of air as an oxygen carrier, $L_{min}$ is also referred to as the minimum air quantity.

From the WO 2006/061228 A1 a method for determining the air number of a burner for a fuel cell heating device is known, in which beside the known flame ionization current measurement used in the burner technology, further parameters are additionally determined to estimate the fuel gas composition and consequently the air number. However, the parameters are based on the gas quantity converted in the device on whose determination no statement can be made a priori.

From the EP 1 923 634 A1 a method for regulating a fuel gas air mixture of a heating device by means of an output temperature measurement is known, in which the required fuel gas volume flow or mass flow is determined on the assumption of a burner load and the load dependent burner temperature or the desired flame temperature is determined on consideration of the combustion air number $\lambda$ of the combustion air volume flow or mass flow, as well as from a characteristic field or from a function. However, there is no indication from where the required fuel gas flows and air volume flows and/or mass flows are known for such a regulation in the case of varying fuel gas qualities.

From the EP 2 574 918 A1 a method of determining physical gas properties of gas mixtures for the correlation of parameters of the gas mixture relevant to combustion processes is known. Hereby, amongst other things, the density, the heat capacity, the mass flow or volume flow of a gas is determined by means of a first sensor. Moreover, the thermal conductivity of the gas is separately measured with a second sensor, the second sensor being a micro thermal sensor.

In the following, the following one dimensional thermal conductivity equation describing the thermal sensor system is assumed (Kerson Huang: *Statistical Mechanics*, 2. edition, John Wiley & Sons, New York 1987, ISBN 0-471-85913-3).

$$\frac{c_p}{\kappa} \cdot \rho v_x \cdot \frac{d}{dx} T = \nabla^2 T + \frac{1}{\kappa} \Theta, \qquad (2)$$

where
- $v_x$ is the component of the mean flow velocity (speed vector) in the x-direction, this means along the gas flow direction;
- T is the temperature;

$$\frac{d}{dx} T$$

is the temperature gradient;
- $c_p$ is the thermal capacity of the gas at constant pressure;
- $\rho$ is the density;
- $\kappa$ is the thermal conductivity of the gas;
- $\nabla^2 T$ is the Laplace operator applied on the temperature T; with $$\nabla^2 = \left(\frac{d}{dx}\right)^2 + \left(\frac{d}{dy}\right)^2 + \left(\frac{d}{dz}\right)^2.$$

Since the gas (gas flow) only flows in the x-direction the components $v_y$ and/or $v_z$ in the y- and the z-direction respectively of the mean flow velocity of $\vec{v}$ are assumed to be zero. $\Theta$ having the unit Watts/m³ describes the source term of the heating element. The source term is brought about by the hot wire of a hot wire anemometer in the thermal method, with the hot wire anemometer introducing thermal energy into the system. The conversion of mean flow velocity into the volume flow is in this connection provided by the (cross-sectional) geometry of the supplying gas line.

If one now relates equation (1) to a combined fuel gas-oxygen carrier calibrated with reference to a calibrated gas (CalGas) and finally impinges the combined fuel gas-oxygen carrier with a different fuel gas mixture (gas), then the following lambda value $\lambda_{actual}$ is set on its own $$\lambda_{actual} = r_{id\_CalGas} \cdot (1+\Delta(\%))/L_{min\_Gas}, \quad (3)$$

where the fuel gas error $\Delta$ relates to the difference between the desired value set by the device with respect to the effectively present fuel gas flow. If in this connection too much trough flow is indicated, then less fuel gas effectively flows which leads to an increase of the oxygen carrier/fuel gas ratio r.

Figure 2:
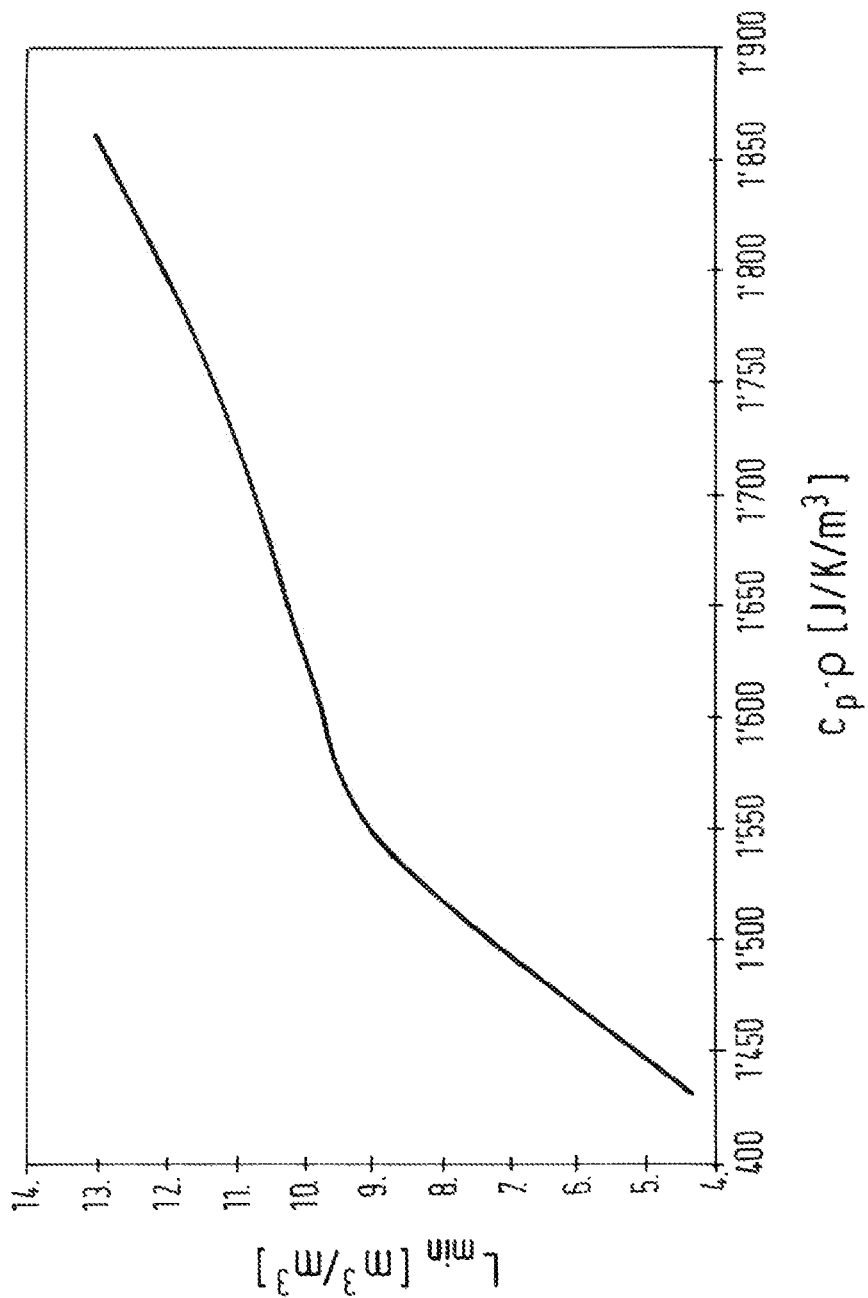

On the other hand, the determination of the ideal lambda value $\lambda_{id}$ and the minimum oxygen carrier requirement $L_{min}$ can take place by means of a correlation of one of the sizes $\kappa$, $c_p$, and/or $\rho$ or of a combination of these parameters on the basis of equation (2) of the thermal sensor system, such as is, for example, shown in FIG. 2 for $L_{min}$ as a function of the product of the thermal capacity and the density $c_p \cdot \rho$ or in FIG. 2a for $\lambda_{id}$ as a function of the thermal conductivity $\kappa$ for the field of application of natural gases. Then the equation for the setting of the lambda value $\lambda_{actual}$ which is analogous to equation (3) reads like $$\lambda_{actual} = r_{id\_corr} \cdot (1+\Delta(\%))/L_{min\_Gas}, \quad (4)$$

having the same effect of an error $\Delta$ in the flow determination as in equation (3), where $r_{id\_corr} = L_{min\_corr} \cdot \lambda_{id\_corr}$ is r analog to equation (1). Errors in the correlated lambda value $\lambda_{id\_corr}$ and in the correlated minimum oxygen carrier requirement $L_{min\_corr}$ tog ether with the flow error can have effects on the currently present fuel gas quality in a damping or amplifying manner with respect to the deviation of the current lambda value having regard to the ideal lambda value $\lambda_{actual} - \lambda_{id}$ which has a positive or negative effect on the efficiency and the operational safety of the energy converter plant in dependence on the selected correlation.

For this reason it is the object of the invention to provide a method, as well a thermal sensor and a regulation apparatus for the combined controlled regulation of fuel gas-oxygen carriers of gas operated energy converter plants which enable an energetically efficient conversion of the supplied fuel gas and a stable operation for a varying fuel gas quality.

In accordance with the invention this object is satisfied with respect to the method by a method having the features in accordance with claim 1. With respect to the sensor this object is satisfied by a sensor having the features in accordance with claim 9 and with respect to the regulation apparatus is satisfied by a regulation apparatus having the features in accordance with claim 12.

In the method for the combined controlled regulation of fuel gas-oxygen carriers of a gas operated energy converter plant, the mass or volume through flow of the fuel gas and/or of the oxygen carrier is detected in order to regulate the mixing ratio r of fuel gas to oxygen carrier. The method is characterized in that at least two physical parameters of the fuel gas are determined using a micro thermal sensor, wherein the first parameter comprises the mass flow and/or volume through flow of the fuel gas and the second parameter comprises the thermal conductivity and/or the thermal capacity; and in that a desired value for the mixing ratio is determined from the physical parameters, said desired value depending on the fuel gas or on the composition of the fuel gas and in this way to use the desired value for the regulation of the mixing ratio. In other words the at least two physical parameters of the fuel gas are determined by means of the same micro thermal sensor.

It has now been found starting from equations (3) and (4) respectively—in contrast to the prejudice present in the prior art such as e.g. described in the EP 2 574 918 A1—that the ratio of the two parameters can reliably be determined with a micro thermal sensor. Thus no other sensor type and in this way no separate sensor is required for the first parameter, since the impact of the error $\Delta$ can be correspondingly compensated, such as has been illustrated in the foregoing with regards to equations (3) and (4). Thus the difference between the lambda value to be set and the ideal lambda value of the fuel gas on which the varying fuel gas quality is based can be kept small in order to achieve an application specific favorable process point. It can furthermore be ensured that the difference never becomes negative in order to not endanger the operational safety.

The at least two physical parameters which were determined with the same micro thermal sensor are advantageously used both for the fuel gas quality determination and for the fuel gas flow determination.

This has the advantage that the two parameters can be determined with the same micro thermal sensor resulting in a more cost effective apparatus, as merely one sensor is required. Moreover, if necessary, merely one sensor has to be calibrated.

In an advantageous embodiment of the method the two physical parameters are, which were determined with the same micro thermal sensor, drawn upon in order to, on the one hand, determine the ideal lambda value $\lambda_{id}$ and the minimum oxygen carrier requirement $L_{min}$ by means of a correlation and, on the other hand, to determine the mass flow and/or the volume flow of the fuel gas.

The determination of the physical parameters and the thereto correlated sizes can, for example, be related to a calibration gas, wherein the deviation of the calibrated lambda value $\lambda_{CalGas}$ with respect to the ideal lambda value $\lambda_{id}$ is compensated by the through flow determination error coupled thereto.

The physical parameters and the sizes correlated therefrom, however, can also be newly determined in part for an arbitrary fuel gas and the remaining parts can be taken on by the calibration gas, wherein the deviation of the lambda value to be set $\lambda_{actual}$ with respect to the ideal lambda value $\lambda_{id}$ is at least partly by compensated the through flow determination error coupled thereto. In this connection, for example, the thermal capacity and/or the thermal conductivity of the calibration gas can be used.

In a further advantageous embodiment of the method the physical parameters and the sizes correlated therefrom for an arbitrary fuel gas can be totally taken on from the calibration gas, wherein the deviations of the lambda value to be set $\lambda_{actual}$ with respect to the ideal lambda value $\lambda_{is}$ is at least partly compensated by the through flow determination error coupled thereto.

Independent of the variant of the method the energy converter plant can be a fuel cell plant, in particular a fuel cell plant having high temperature fuel cells of the SOFC type, a cogeneration plant, a gas motor, a heating device respectively a gas furnace, a gas operated heat pump, a warm water generator and/or a gas operated current generation plant or a combination thereof.

The sensor in accordance with the present invention for the combined controlled regulation of fuel gas-oxygen carriers of a gas operated energy converter plant is equipped with an evaluation and regulation unit which is configured for carrying out a method for the combined controlled regulation of fuel gas-oxygen carriers in accordance with the above description and comprises a micro thermal hot wire anemometer which can be impinged by a fuel gas in order to determine at least two physical parameters of the fuel gas, for example, the thermal conductivity and/or the thermal capacity as a first physical parameter and, for example, the mass flow and/or volume flow of a micro thermal method as a second physical parameter and to determine a desired value for the mixing ratio from the physical parameters, said desired value being dependent on the fuel gas or on the composition of the fuel gas and in this way to regulate the corresponding fuel gas quantity and/or the oxygen carrier quantity.

In an advantageous embodiment the sensor comprises two micro thermal hot wire anemometers, a first micro thermal hot wire anemometer for the fuel gas and a second micro thermal hot wire anemometer for the oxygen carrier.

In a further advantageous embodiment the at least one micro thermal hot wire anemometer is designed as an integrated CMOS hot wire anemometer.

Independent of the embodiment the sensor can be adapted to regulate the fuel gas quantity and/or the oxygen carrier quantity by means of traditional thermal mass flow meters and/or regulators.

The invention further comprises a regulation apparatus for the combined controlled regulation of fuel gas-oxygen carriers of a gas operated energy converter plant, wherein the regulation apparatus includes a sensor for the combined controlled regulation of fuel gas-oxygen carriers in accordance with the above description and at least one valve in order to regulate the fuel gas quantity and/or the oxygen carrier quantity or quantities.

In an advantageous embodiment of the regulation apparatus for the combined controlled regulation of fuel gas-oxygen carriers of a gas energy converted plant the valve is configured as a mixing valve.

The invention further comprises a fuel cell plant, in particular a fuel cell plant having high temperature fuel cells of the SOFC type, having a regulation apparatus for the combined controlled fuel gas-oxygen carriers in accordance with the above description.

The idea of the invention is thus the provision of a method, a sensor and a regulation apparatus for the energetically efficient conversion of the supplied fuel gas, such as e.g. natural gas and for ensuring the stability and lifetime of gas operated energy converter plants having a combined controlled regulation of fuel gas-oxygen carriers, wherein, on the one hand, physical parameters, such as e.g. the ideal lambda value $\lambda_{id}$ and the minimum oxygen carrier requirement $L_{min}$ are determined with a thermal sensor and, on the other hand, the through flow quantity in fuel gas-oxygen carriers compound is measured for a varying fuel gas quality using the same sensor in order to regulate the gas operated energy converter plant to the ideal mixing ratio $r_{id}$.

The method, the thermal sensor and the regulation apparatus for the combined controlled regulation of fuel gas-oxygen carriers of gas operated energy converter plants in accordance with the present invention have the advantage that they can be realized and/or manufactured comparatively simply and cost-effectively and that the difference between the lambda value to be set and the ideal lambda value of the fuel gas based thereon for a varying fuel gas quality can be kept small, on the one hand and in order to achieve a favorable process point from an application specific point of view and, on the other hand, never becomes negative so as not to endanger the operational safety.

Further advantages become evident from the following description. Advantageous embodiments of the invention are to be found in the subordinate claims.

Figure 3:
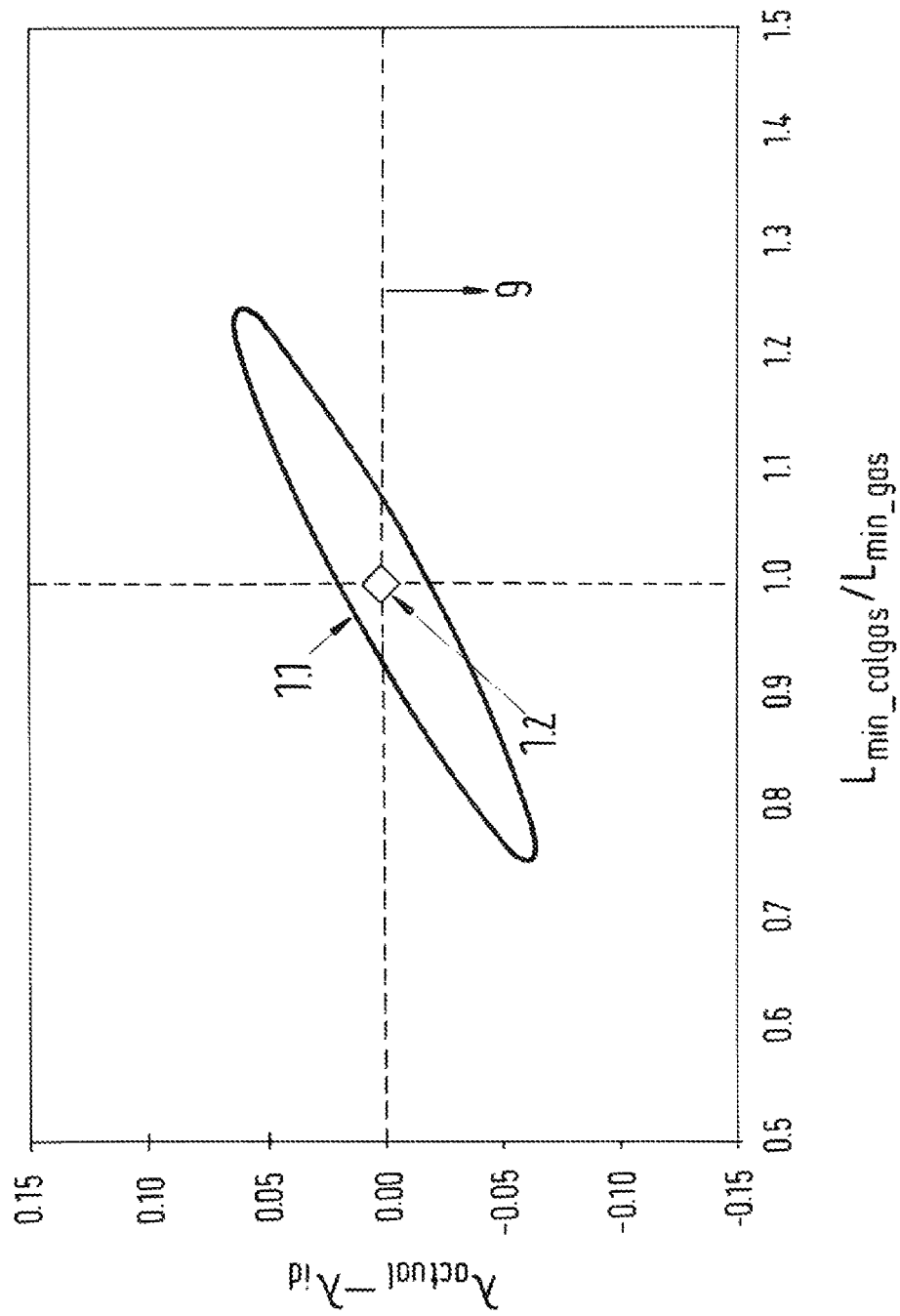
Figure 4:
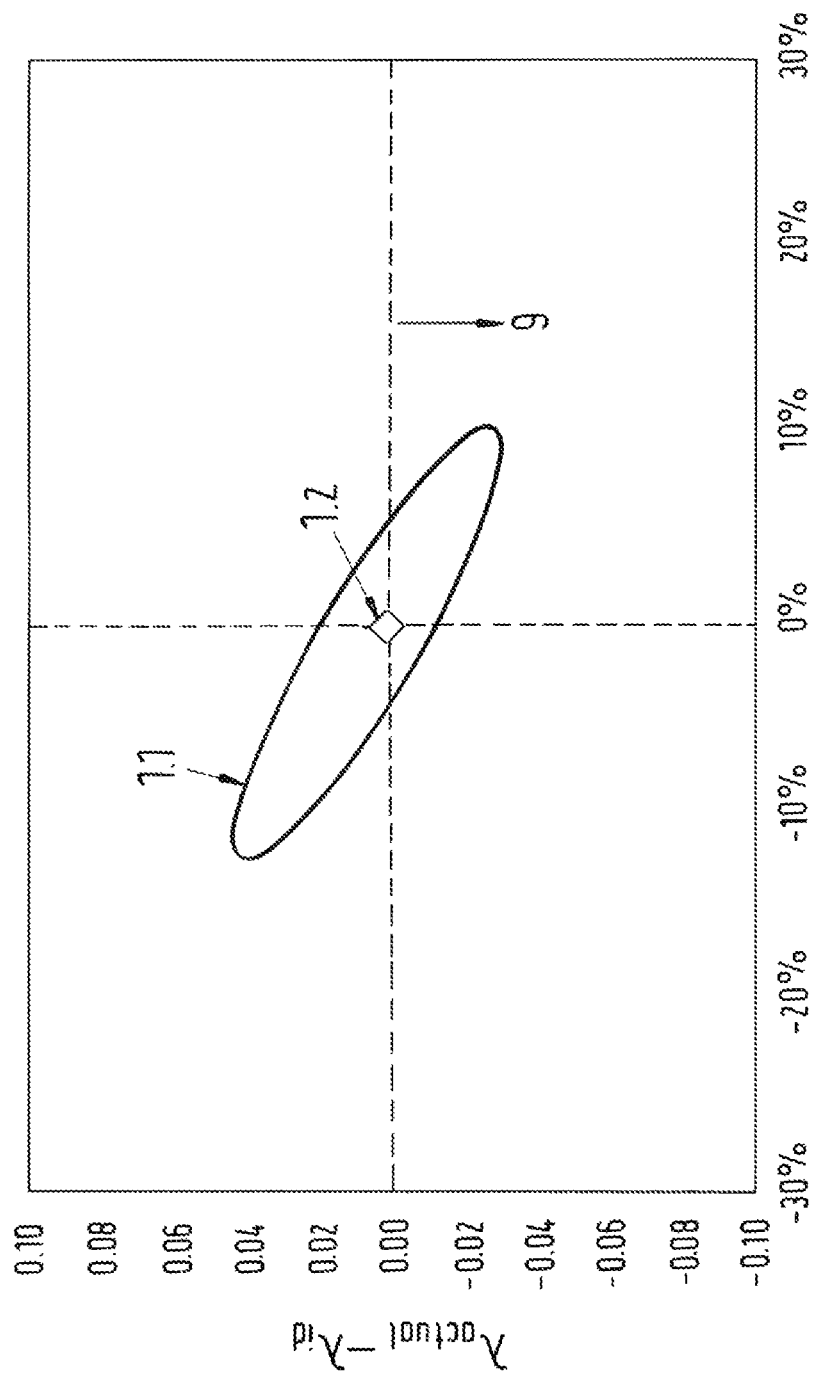
Figure 5:
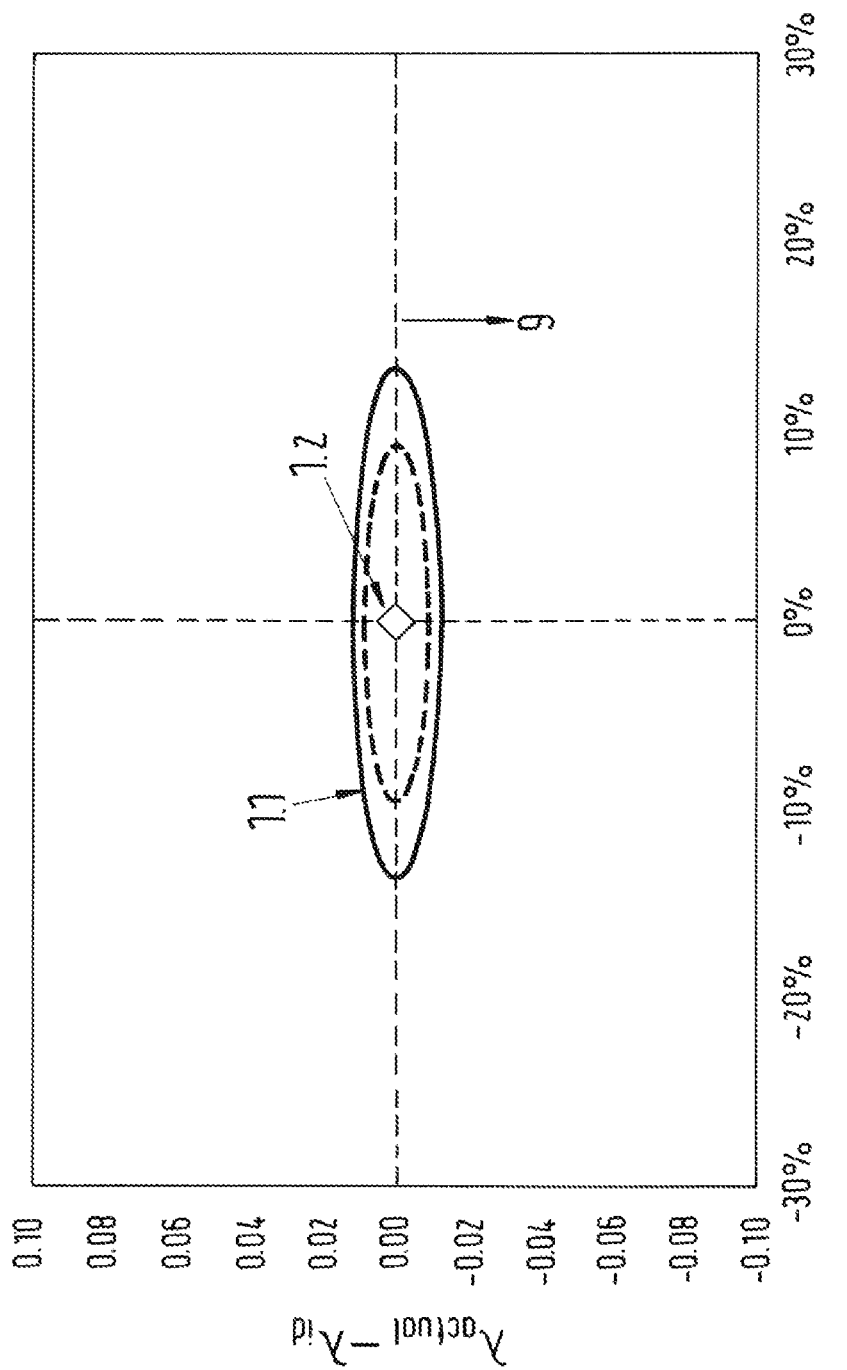
Figure 6:
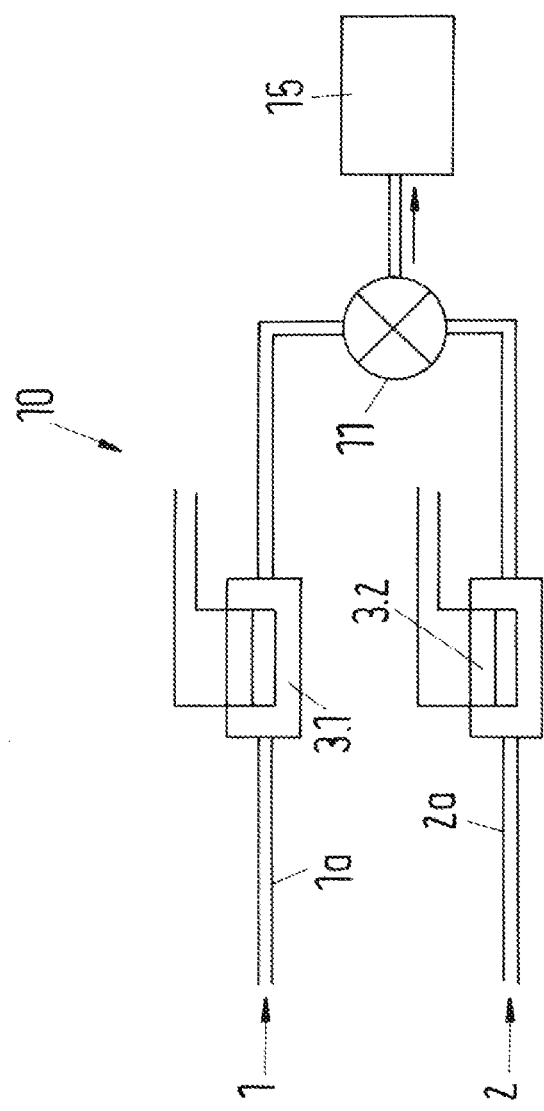
Figure 7:
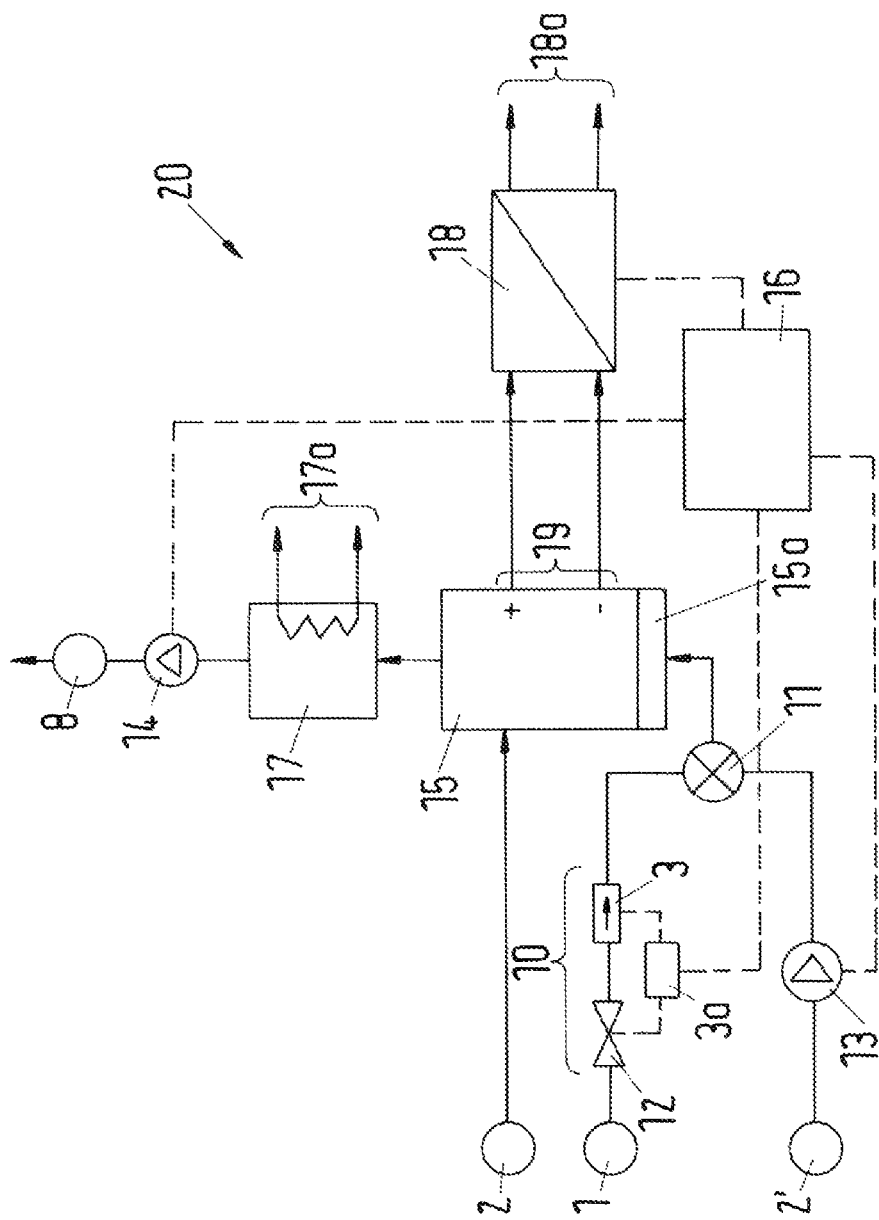
Figure 7A:
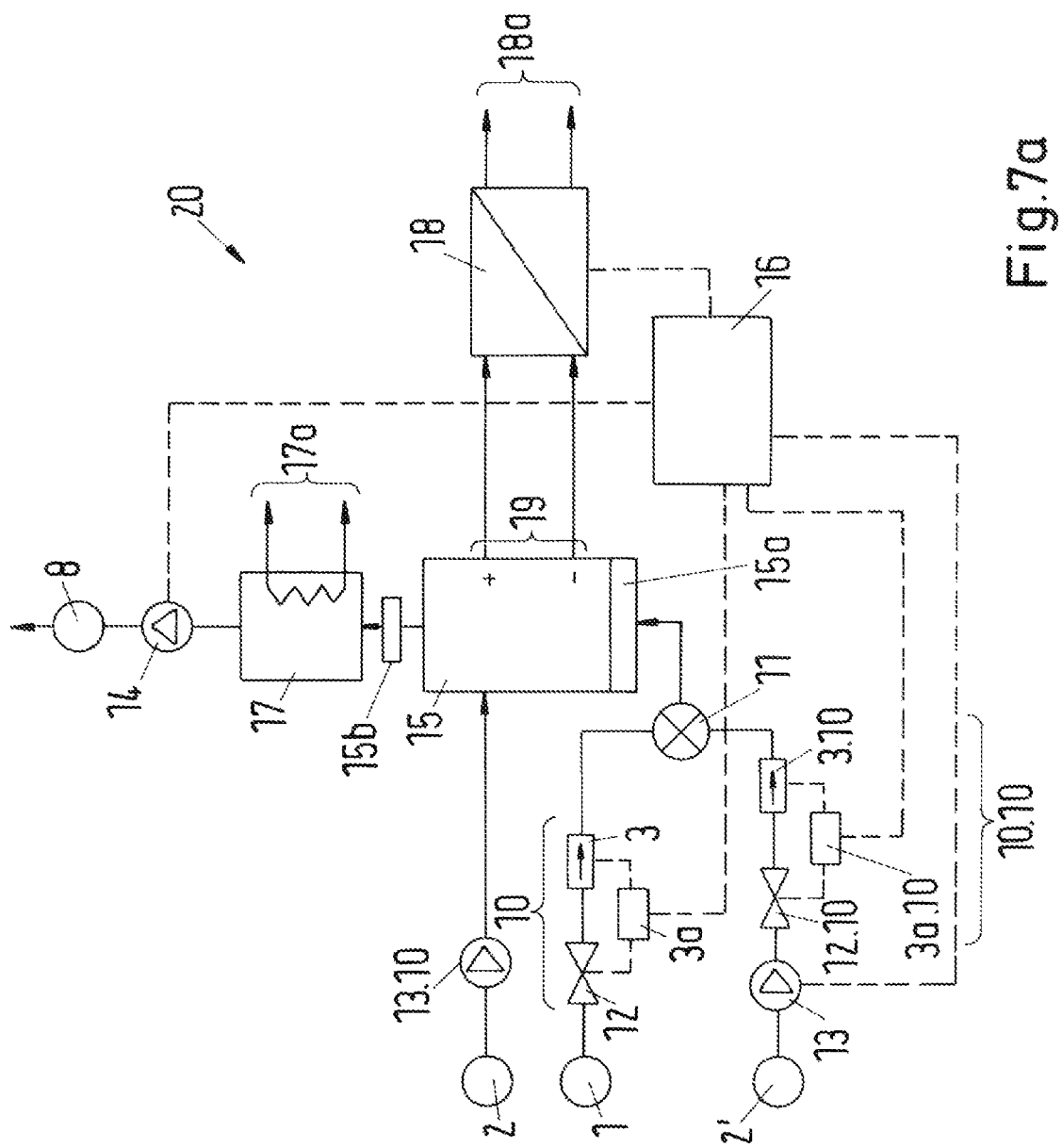

The invention will be described in detail in the following with reference to the drawings. There is shown FIG. 1 a sensor head of an integrated CMOS anemometer;

FIG. 2 the correlation between minimum oxygen carrier requirement and the product of thermal capacity and density of the fuel gas;

FIG. 2a the correlation between an ideal ratio of oxygen carrier amount to fuel gas amount and the thermal conductivity of the fuel gas;

FIG. 3 the deviation of the lambda value to be set with respect to the ideal lambda value as a function of the oxygen carrier requirement on lack of knowledge of the fuel gas quality, but for an error free gas flow determination in the case of an SOFC fuel cell having partial oxidation in comparison to a calibration gas;

FIG. 4 the deviation of the lambda value to be set with respect to the ideal lambda value as a function of the flow error for a common mass flow meter and/or regulator in the case of an SOFC fuel cell having partial oxidation in comparison to a calibration gas;

FIG. 5 the deviation of the lambda value to be set with respect to the ideal lambda value as a function of the flow error for a micro thermal sensor in the case of an SOFC fuel cell having partial oxidation in comparison to a calibration gas;

FIG. 6 an embodiment of a simple design of a regulation apparatus in accordance with the invention for the combined controlled regulation of fuel gas-oxygen carriers of an energy converter plant;

FIG. 7 an embodiment of a fuel cell plant having a combined controlled regulation of fuel gas oxygen carriers in accordance with the present invention;

FIG. 7a a different specific embodiment in accordance with FIG. 7.

For a known thermal conductivity κ on the left side of the equation (2) an equal role is given to the volume and/or mass flow of $v_x$ or respectively $\rho \cdot v_x$, the density $\rho$ and the thermal capacity $c_p$ in the prefactor on the solution of equation (2).

$$c_p \cdot \rho \cdot v_x, \qquad (5).$$

For determining the mass flow the knowledge of the thermal capacity $c_p$ of the fuel gas is thus required and the product $c_p \cdot \rho$ is used for determining the volume flow. Since in accordance with the invention the same sensor is used both for the fuel gas quality determination and for the fuel gas flow determination a fuel gas error is found e.g. then when the thermal capacity $c_p$ of the fuel gas or the product $c_p \cdot \rho$ in equation (2) and/or in the prefactor of equation (5) is only known in an imprecise manner.

If vice versa only an as precise as possible trough flow measurement is considered in a combined controlled regulation of fuel gas-oxygen carriers and if no information is present on a fuel gas quality, such as e.g. on use of an ultrasonic trough flow meter the fuel gas flow error Δ in equation (3) indeed becomes zero; however, the lambda value $\lambda_{actual}$ to be set can strongly vary due to the variations in $L_{min\_gas}$ which can lead to the formation of soot in the energy converter plant when $\lambda_{actual}$ is smaller than the ideal lambda value $\lambda_{id}$.

FIG. 2a shows the correlation between an ideal ratio of oxygen carrier amount to fuel gas amount and the thermal conductivity of the fuel gas for a fuel cell plant having high temperature fuel cells of the SOFC-type.

FIG. 3 shows a deviation $\lambda_{actual}-\lambda_{id}$ of the lambda value to be set with respect to the ideal lambda value as a function of the oxygen carrier requirement $L_{min\_calgas}/L_{min\_gas}$ on the uncertainty of the fuel fuel gas quality, but for an error free gas flow determination in the case of an SOFC fuel cell having partial oxidation in comparison to a calibration gas. The value of the deviation 1.2 for the calibration gas is zero while the value of the deviation 1.1 for natural gas for $\lambda_{actual}-\lambda_{id}<0$ extends into the field 9 in which the danger of sooting arises.

Commercially available thermal "mass flow meters" and/or "mass flow regulators" are named with reference to the fact that the thermal conductivity is indeed unknown for a given fuel gas, but is constant apart from a temperature dependence which is also true for the thermal capacity. In this case $$\rho \cdot v_x, \quad (6)$$

the mass flow is thus the parameter which is deterministic for the system, which parameter can then be determined through the calibration of the unknown constant parameters $\kappa$ and $c_p$ of a calibration gas. Since the hot wire for these devices is either wound around the measurement capillary supplying the fuel gas or, in the case of heating elements and guide elements project directly into the fuel gas flow having a metal jacket, it is thus true for both variants that they have a high thermal heat conductivity in comparison to the supplied fuel gas which renders the influence of the fuel gas negligible. In this way, however, also the possibility is at the same time excluded from using the information on the thermal conductivity of an unknown fuel gas in order to apply corresponding corrections for a varying fuel gas quality on the combined controlled regulation of fuel gas-oxygen carriers. The influence of the thermal capacity $c_p$ by comparison is generally associated with the fuel gas which is expressed therein that the manufacturers of thermal mass flow meters and/or mass flow regulators provide conversion tables for different fuel gasses for the flow which are based on the thermal capacity (prefactor of equation (5)).

It is different on the use of a micro thermal sensor, such as e.g. an integrated CMOS hot wire anemometer. With respect to this technology reference is made to D. Matter, B. Kramer, T. Kleiner, B. Sabbattini, T. Suter, "Mikroelektronische Haushaltsgaszähler mit neuer Technologie", (microelectronic household gas counters with new technology) Technisches Messen (technical measurements) 71, 3 (2004), pages 137-146.

A sensor head of an integrated CMOS hot wire anemometer is shown in FIG. 1. The CMOS hot wire anemometer 3 of FIG. 1 can in use be arranged in a gas line 1a and can be impinged with a fuel gas and, as the case may be, can also be impinged with an oxygen carrier flow and comprises a substrate 4 which typically includes a membrane 5 having a thickness of a few micrometers. The CMOS hot wire anemometer further comprises two thermal elements 6.1, 6.2 and a heating element 7 which can be arranged between the two thermal elements in the flow direction.

The method using a micro thermal sensor, such as for example an integrated CMOS hot wire anemometer is different from the method of common thermal mass flow measurements in that the actual sensor head having a heating element 7 and temperature feeling elements 6.1, 6.2 is only applied onto a membrane 5 having a thickness of a few micrometers and directly projects into the fuel gas flow 1, wherein the thermal conductivity of the membrane is approximately comparable to that of the fuel gas. For a varying fuel gas quality its influence thus becomes noticeable which reversely enables the determination of the thermal conductivity of the fuel gas. By means of the possibility of the determination of the thermal conductivity any arbitrary thermal process can be copied by means of the micro thermal method. However, also further possibilities of a combined controlled regulation of a fuel gas oxygen are enabled, in that, besides the complete compensation of the influence of the thermal conductivity, only a part or even a completely absent compensation of the latter can be considered, as will be illustrated in the following.

By means of an integrated micro thermal sensor the imaging of, e.g. the functionality of a common thermal mass flow meter is possible with the sole determination of the thermal conductivity $\kappa$ in equation (2), when one does not allow any further information on the thermal capacity $c_p$ other than that of the calibration gas to be used. With respect to the lambda value, the flow error to be set in this case is positive with respect to the desired aim of an as small as possible only positive deviation with reference to the idela value (equation (3)).

FIG. 4 shows the deviation $\lambda_{actual}-\lambda_{id}$ of the lambda value to be set with respect to the ideal lambda value as a function of the flow error $\Delta$ for a commercially available mass flow meter and/or mass flow regulator in the case of an SOFC fuel cell having partial oxidation in comparison to a calibration gas. The value of the deviation 1.2 for the calibration gas is zero while the value of the deviation 1.1 for natural gases for $\lambda_{actual}-\lambda_{id}<0$ extends into the field 9 in which the danger of sooting is present.

The knowledge of the thermal capacity $\kappa$ brings about a further improvement, since the information on $c_p$ of an unknown fuel gas can be obtained in order to carry out a mass flow measurement independent of the fuel gas quality which was previously not possible using a traditional device.

FIG. 5 shows the deviation $\lambda_{actual}-\lambda_{id}$ of a lambda value to be set with respect to the ideal lambda value as a function of the flow error $\Delta$ for a micro thermal sensor in the case of an SOFC fuel cell having partial oxidation in comparison to a calibration gas. The possible deviation $\lambda_{actual}-\lambda_{id}$ is considerably smaller with respect to the deviation of a commercially available mass flow meter as shown in FIG. 4 and the values of the deviation 1.1 for natural gas for $\lambda_{actual}-\lambda_{id}<0$ extends less far into the field 9 in such a way that the danger of sooting is reduced.

If one takes into account the parameters, such as e.g. the minimum oxygen carrier requirement for this purpose (FIG. 2), which can be correlated by means of an integrated micro thermal sensor then the values of the deviation shown in FIG. 5 for natural gases can be reduced to an even smaller region (dotted ellipse) up to the ideal case where all fuel gases lie at the crossing point of the calibration gas.

In other words the object is satisfied with respect to the method in accordance with the invention by a micro thermal determination of the ideal lambda value $\lambda_{id}$ and the minimum oxygen carrier requirement $L_{min}$ with the simultaneous determination of the trough flow, on the one hand, for achieving the ideal process point from an application specific point of view and, on the other hand, for insuring the operational safety for a varying fuel gas quality, wherein the micro thermal method provides the possibility, in dependence on the type of application of an energy converter plant, to select the degree of accuracy of this determination and in this way the demand in effort and the corresponding costs associated therewith. This can take place in that only a part of the relevant basic parameters of a thermal method, this means the thermal conductivity, the thermal capacity, the mass flow or the volume flow are used and the error compensating properties of the method resulting therefrom are utilized or in that the said parameters are determined and are drawn upon for the correlation of $\lambda_{id'}$ and $L_{min}$.

In the method in accordance with the invention the ideal lambda value $\lambda_{id}$ and the minimum oxygen carrier requirement $L_{min}$ are thus determined in the kind and manner such that a lambda value is set for which the difference with respect to the ideal lambda value is as small as possible for a varying fuel gas quality on the basis of the fuel gas, on the one hand, for achieving the application specific ideal process point and, on the other hand, never becomes negative in order to not endanger the operational safety.

In accordance with an advantageous embodiment of the invention the basic parameters thermal conductivity, thermal capacity, mass flow or volume flow are determined and by means of the micro thermal method $\lambda_{id}$ and $L_{min}$ are correlated therefrom which leads to a maximum efficiency and operational safety of the system.

In accordance with a further advantageous embodiment of the invention the influence of the basic parameters thermal conductivity, thermal capacity, mass flow or volume flow are only partly compensated by means of the micro thermal method, whereby a certain lambda value $\lambda_{actual}$ is set, with the simultaneously set through flow error effecting the deviation with respect to the ideal lambda value $\lambda_{id}$ in a damping manner.

In accordance with a further advantageous embodiment of the invention the influence of the basic parameters thermal conductivity, thermal capacity, mass flow or volume flow are not compensated by means of the micro thermal method, whereby a certain lambda value $\lambda_{actual}$ is set, with the simultaneously setting through flow error itself in this case effecting the deviation with respect to the lambda value $\lambda_{id}$ in a damping manner which leads to a very cost-effective method.

The sensor in accordance with the present invention for the combined controlled regulation of fuel gas-oxygen carriers of a gas operated energy converter plant is equipped with an evaluation and regulation unit which is configured for carrying out a method in accordance with the present invention or one of the above described embodiments of the same and comprises a micro thermal hot wire anemometer which can be impinged by a fuel gas in order to determine at least two physical parameters of the fuel gas, for example, the thermal conductivity and/or thermal capacity as a first physical parameter and, for example, the mass flow and/or volume flow of a micro thermal method as a second physical parameter and to determine a desired value for the mixing ratio from the physical parameters, said desired value being dependent on the fuel gas or on the composition of the fuel gas and in this way to regulate the corresponding fuel gas quantity and/or the oxygen carrier quantity.

A micro thermal sensor in accordance with the invention for the combined controlled regulation of fuel gas-oxygen carriers of an energy converter plant works in accordance with the method in accordance with the invention, for example, with a sensor block having an integrated micro thermal CMOS hot wire anemometer passed which the fuel gas flows, by means of the measurement of two temperatures upstream and downstream of the hot wire, as shown in FIG. 1. The temperature information of upstream and downstream lying temperature feelers permits the determination of parameters on the right hand side of equation (2) with the aid of the solution of equation (2) and separately permits the determination of the thermal conductivity of the fuel gas mixture. By means of the thus determined parameters the fuel gas quantity and/or oxygen carrier quantity is/are regulated.

An embodiment of a simple assembly of a regulation apparatus in accordance with the invention for the combined controlled regulation of fuel gas-oxygen carriers of an energy converter plant is shown in FIG. 6. The regulation apparatus 10 in accordance with the invention for the combined controlled regulation of fuel gas-oxygen carriers of a gas operated energy converter plant includes at least one micro thermal sensor 3.1, a simple flow sensor 3.2 for the combined controlled regulation of fuel gas-oxygen carriers in accordance with the above description and at least one valve, in particular a regulated mixing unit 11 in order to regulate the fuel gas quality and/or the oxygen carrier quantity.

In a further embodiment of the regulation apparatus fuel gas 1 flows out of the gas line 1a and oxygen carriers 2 flow out of the supply line 2a for the oxygen carrier both initially flowing trough a respective sensor 3.1 and/or 3.2 having an integrated CMOS hot wire anemometer for the measurement of at least two physical parameters, wherein the first parameter, in particular comprises the mass flow and/or volume trough flow and the second parameter, for example, comprises the thermal conductivity and/or the thermal capacity of the fuel gas, from which the ideal lambda value $\lambda_{id}$ and the minimum oxygen carrier requirement $L_{min}$ can be derived in order to regulate the correct mixing ratio between fuel gas and oxygen carriers. Fuel gas and oxygen carriers can be combined in a mixing unit 11, in particular in a mixer 11 and can be forwarded, for example, to a gas operated energy converter 15.

The invention further comprises a fuel cell plant, in particular a fuel cell plant having high temperature fuel cells of the SOFC type having a regulation apparatus for the combined controlled regulation of fuel gas-oxygen carriers in accordance with the above description.

An embodiment of a fuel cell plant having a combined controlled regulation of fuel gas-oxygen carriers in accordance with the present invention is shown in FIG. 7.

The fuel cell plant in this embodiment includes a fuel cell stack 15, which can for example be assembled from high temperature fuel cells of the SOFC type ("Solid Oxide Fuel Cell") which are typically operated at a temperature of 600° C. to 1000° C. and which enables the use of energy of a fuel trough an energy conversion. In this connection both electrical energy which is produced due to electrochemical processes and also thermal energy which arises in the form of hot exhaust gases of the processor can be used. During operation the gas like flows of a fuel gas 1, in the case of natural gas a reformed fuel gas, and oxygen carriers 2 are guided separately trough the cells. The oxygen carriers 2, in particular include environmental air.

Normally the gas used as a fuel gas will include methane (e.g. natural gas) which is guided through a reformer 15a prior to the entrance into the cells and is converted there for example, in contrast to FIG. 7, also endothermically on the supply of process heat, into the reducing components hydrogen and carbon monoxide and others. The hot exhaust gas can advantageously be used in the form of starting heat as a source for the process heat required in the reformer.

The fuel cell plant additionally includes a regulation apparatus 10 for the combined controlled regulation of fuel gas-oxygen carriers which, as shown in FIG. 7, can be arranged in the supply line for the fuel gas 1 in order to control or to regulate the fuel gas quantity and possibly also the oxygen carrier quantity. In the shown embodiment the regulation apparatus comprises at least one micro thermal sensor 3 in accordance with the above description and at least one regulation valve 12, wherein the micro thermal sensor is connected to the regulation valve, for example, via an evaluation and regulation unit 3a which is configured for carrying out a method in accordance with the present invention or one of the above described embodiments of the same.

Advantageously the fuel cell plant additionally includes a regulation apparatus 10.10, moreover a mass flow meter 3.10 and/or a mass flow regulator 3a.10 and/or a regulation valve 12.10 which can be arranged in the supply line for the oxygen carrier 2' in order to control and/or to regulate the oxygen carrier quantity. In the embodiment shown in FIGS. 7 and 7a respectively a blower 13 is arranged in the supply line for the oxygen carrier 2' for the increase of pressure in order to control and/or to regulate the oxygen carrier quantity.

Furthermore, a mixing apparatus 11 is advantageously provided following the combined controlled regulation of fuel gas-oxygen carriers in order to mix the fuel gas and the oxygen carriers before these are supplied to the reformer 15a. The required lambda value of the fuel gas-oxygen carrier mixture depends on the reforming process. For a typical reforming process without the supply of water the required lambda value lies between 0.2 and 0.5, in particular between 0.24 and 0.30.

The fuel cells are typically operated at a lambda value between 1.4 and 5, in particular between 1.7 and 3. A separate supply line for the fuel cell stack is provided for the supply of the oxygen carriers 2 required for this purpose, as is shown in FIG. 7.

A post combustion unit followed by a heat exchanger 17 is connected Downstream of the fuel cell stack 15 in which heat exchanger the heat of the hot exhaust gases from the fuel cell stack is removed. The heat exchanger 17 is advantageously connected to a heating circuit 17a. The exhaust gases 8 can subsequently be guided into the free air or the residual oxygen in the exhaust gases can be used in an additional burner which is not shown in FIG. 7.

If required and in an advantageous embodiment an exhaust gas blower 14 can be arranged at the output side of the fuel stack 15 or of the heat exchanger 17 by means of which the quantity of oxygen carriers trough the fuel cell stack and in this way optionally also the temperature in the fuel cell stack can be controlled and/or regulated. The blower can alternatively also be provided at the input side of the fuel cell stack in the branch 2 (blower 13.10).

In an advantageous embodiment the fuel cell plant 20 further comprises a voltage transformer or a varying current converter 18, for example, a regulatable voltage converter or a regulatable varying current converter, which is connected to the output 19 of the fuel cell stack 15. Advantageously the voltage converter or the varying current converter is connected to a current grid 18a in order to introduce the current produced in the fuel cell stack into the current grid.

In a further advantageous embodiment the fuel cell plant 20 moreover comprises a control unit 16 which can optionally be connected to the regulation apparatus 10 and/or to the blower 13 and/or to the exhaust gas blower 14 and/or to the voltage converter or to varying current converter 18.

FIG. 7a finally shows a different specific embodiment which is only different from that of FIG. 7 in that a further regulation apparatus 10.10 having a regulation valve 12.10, a regulation unit 3a.10 and a flow sensor 3.10, possibly configured as a micro thermal sensor, is also installed in the supply line for the oxygen carriers 2a in this example, and a blower 13.10 is also additionally provided in the supply line for the oxygen carriers 2 as an option for the exhaust gas blower 14.

The method, the thermal sensor and the regulation apparatus for the combined controlled regulation of fuel gas-oxygen carriers of gas operated energy converter plants in accordance with the present invention have the advantage that the difference between the lambda value to be set and the ideal lambda value of the fuel gas of varying fuel gas quality can be maintained comparatively small which permits the determination of an application specific ideal point of operation. At the same time a safe operation is enabled thanks to the correlation of the ideal lambda value $\lambda_{id}$ and the minimum oxygen carrier requirement $L_{min}$ by means of the measured physical parameters.

The invention claimed is:

1. A method for the combined controlled regulation of fuel gas-oxygen carriers of a gas operated energy converter plant,
   wherein a mass or volume through flow of a fuel gas and/or of an oxygen carrier is detected in order to regulate a mixing ratio of the fuel gas to the oxygen carrier,
   wherein at least two physical parameters of the fuel gas are determined using a micro thermal sensor,
   wherein a first parameter, of the al least two physical parameters, comprises the mass flow and/or volume through flow of the fuel gas and a second parameter, of the at least two physical parameters, comprises a thermal conductivity or the thermal conductivity and a thermal capacity; and in that a desired value for the mixing ratio is determined from the at least two physical parameters which depends on the fuel gas or on a composition of the fuel gas and which is used for the regulation of the mixing ratio,
   wherein the thermal conductivity, which is determined using the micro thermal sensor, is used to determine an ideal lambda value based on a first correlation between the thermal conductivity and ideal lambda values, and is used to determine a minimum oxygen carrier demand based on a second correlation between the thermal conductivity and minimum oxygen carrier demand values, and
   wherein the at least two physical parameters, which were determined using the same micro thermal sensor, are used to determine a mass flow and/or volume flow of the fuel gas.

2. The method in accordance with claim 1, wherein the at least two physical parameters, which were determined using the same micro thermal sensor, are used for fuel gas quality determination and for fuel gas flow determination.

3. The method in accordance with claim 1, wherein the determination of the at least two physical parameters and of sizes correlated therefrom are related to a calibration gas, and wherein a deviation of a calibrated lambda value with respect to the ideal lambda value is partly or completely compensated by means of a through flow determination error coupled thereto.

4. The method in accordance with claim 3, wherein the at least two physical parameters and sizes for an arbitrary fuel gas correlated therefrom is in part newly determined and a remainder is taken over from the calibration gas and wherein a deviation of the lambda value to be set with respect to the ideal lambda value is at least partly compensated by means of the through flow determination error coupled thereto.

5. The method in accordance with claim 4, wherein the thermal capacity and the thermal conductivity are taken over from the calibration gas.

6. The method in accordance with claim 3, wherein the at least two physical parameters and sizes for an arbitrary fuel gas correlated therefrom are taken over completely from the calibration gas and wherein a deviation of the lambda value to be set with respect to the ideal lambda value is at least partly compensated by means of the through flow determination error coupled thereto.

7. The method in accordance with claim 1, characterized in that the energy converter plant is a fuel cell plant, in particular a fuel cell plant having high temperature fuel cells of the SOFC type, a cogeneration plant, a gas motor, a heating device or a gas furnace, a gas operated heat pump, a warm water generator and/or a gas operated current generation plant or a combination thereof.

8. A sensor for the combined controlled regulation of fuel gas-oxygen carriers of a gas operated energy converter plant, comprising an evaluation and regulation unit configured for carrying out the method in accordance with claim 1 and having a micro thermal hot wire anemometer which can be impinged by the fuel gas in order to determine the at least two physical parameters of the fuel gas as well as the mass flow and/or volume flow of a micro thermal method and in order to determine a desired value for the mixing ratio from the at least two physical parameters, said desired value being dependent on the fuel gas or on a composition of the fuel gas and in this way to regulate corresponding fuel gas and/or oxygen carrier quantity.

9. The sensor in accordance with claim 8, wherein the sensor is composed of at least one micro thermal hot wire anemometer for the fuel gas and/or wherein the one micro thermal hot wire anemometer, or in the case that two micro thermal hot wire anemometers are used, both hot wire anemometers, is/are designed as integrated CMOS hot wire anemometers.

10. The sensor in accordance with claim 8, wherein the sensor is configured to regulate the fuel gas quantity and/or the oxygen carrier quantity by means of conventional thermal mass flow meters and/or regulators.

11. A regulation apparatus for the combined controlled regulation of fuel gas-oxygen carriers of a gas operated energy converter plant, wherein the regulation apparatus comprises the sensor in accordance with claim 8 and at least one regulation valve, and a regulated blower in order to regulate the fuel gas quantity and/or the oxygen carrier quantity.

12. The regulation apparatus in accordance with claim 11, wherein the regulation valves are configured as mixing valves of the mixing unit.

13. A fuel cell plant having high temperature fuel cells of the SOFC type, having the regulation apparatus for the combined controlled regulation of fuel gas-oxygen carriers in accordance with claim 11.

* * * * *